United States Patent
Stanley, III

(10) Patent No.: US 6,830,733 B2
(45) Date of Patent: Dec. 14, 2004

(54) ARTIFICIAL FLOWER

(76) Inventor: Virgil E. Stanley, III, 5860 N. Michigan Rd., Indianapolis, IN (US) 46228

( * ) Notice: Subject to any disclaimer, the term of this patent is extended or adjusted under 35 U.S.C. 154(b) by 240 days.

(21) Appl. No.: 10/164,818

(22) Filed: Jun. 7, 2002

(65) Prior Publication Data

US 2004/0028571 A1 Feb. 12, 2004

(51) Int. Cl.[7] .................................................. A62B 7/08
(52) U.S. Cl. ........................... 422/124; 239/27; 239/53; 422/4; 422/5; 422/120; 422/122; 422/123; 422/125
(58) Field of Search ................. 422/120, 122, 422/123, 124, 125, 4, 5; 428/24; 239/53, 27

(56) References Cited

U.S. PATENT DOCUMENTS

| | | |
|---|---|---|
| 355,982 A | 1/1887 | Eggert, Jr. |
| 3,400,890 A | 9/1968 | Gould |
| 3,775,227 A | 11/1973 | Wilbert et al. |
| 4,708,851 A | 11/1987 | Freytag von Loringhoven |
| 4,919,981 A | 4/1990 | Levey et al. |
| 5,077,102 A | 12/1991 | Chong |
| 5,242,111 A | 9/1993 | Nakoneczny et al. |
| 5,437,410 A | 8/1995 | Babasade |
| 5,776,561 A | 7/1998 | Lindauer |
| 5,888,261 A | 3/1999 | Fortune |
| 6,013,524 A | 1/2000 | Friars et al. |
| 6,103,201 A | 8/2000 | Green |
| 6,153,274 A * | 11/2000 | Koo .............................. 428/24 |
| 6,156,088 A * | 12/2000 | Cardarelli .................. 55/385.8 |
| 6,318,876 B1 | 11/2001 | Sigro et al. |
| 6,391,398 B1 | 5/2002 | Pesu et al. |

* cited by examiner

*Primary Examiner*—Krisanne Jastrzab
(74) *Attorney, Agent, or Firm*—Coats & Bennett, P.L.L.C.

(57) ABSTRACT

An artificial flower includes a hollow stem and a flower portion disposed adjacent one end of the hollow stem. A fragrance source is associated with the artificial flower. In one embodiment, the fragrance source is disposed within the hollow stem of the artificial flower and the fragrance source is adapted to emit a fragrance that moves through at least a portion of the hollow stem.

22 Claims, 3 Drawing Sheets

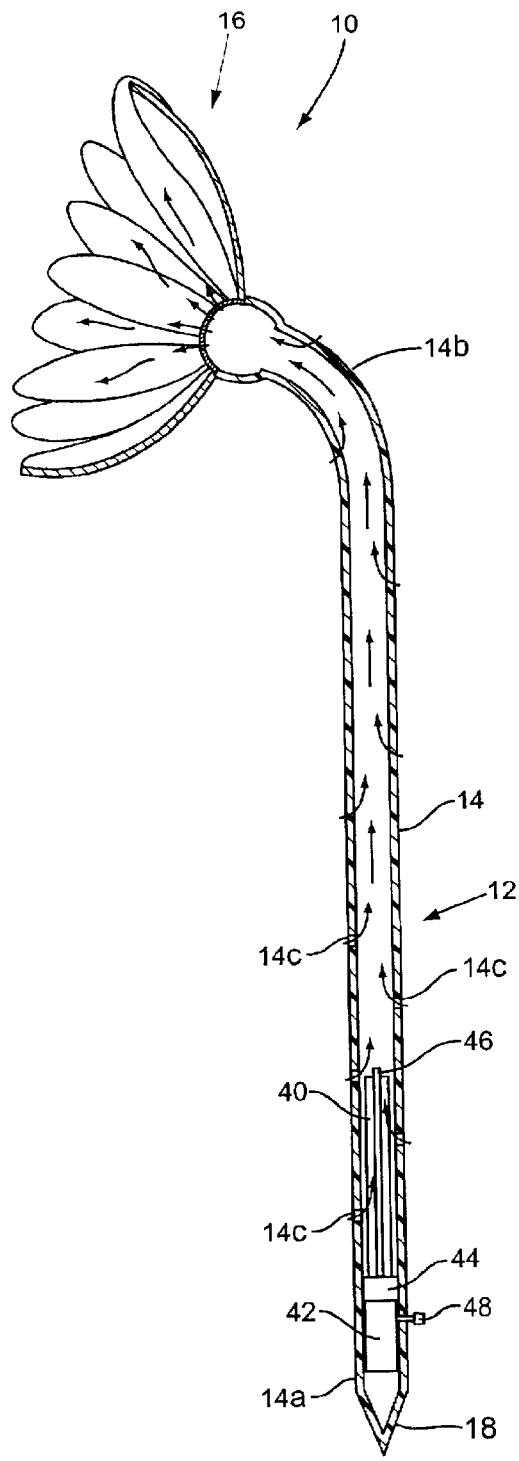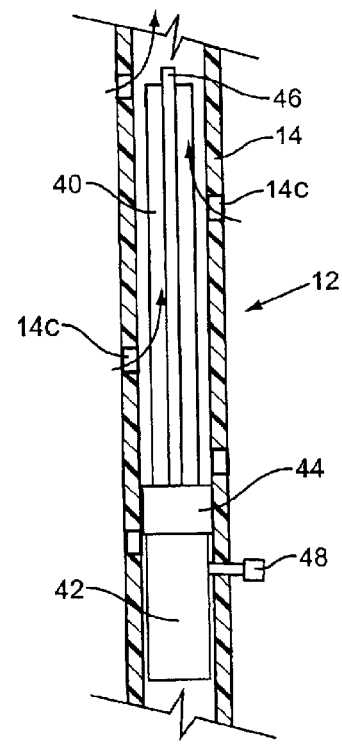
FIG. 2A
FIG. 2

ARTIFICIAL FLOWER

FIELD OF THE INVENTION

The present invention relates to artificial flowers and more particularly to an artificial flower having a fragrance source associated therewith.

BACKGROUND OF THE INVENTION

Artificial flowers are well known and are sold and used throughout the world. What is truly significant about artificial flowers today is how realistic and beautiful artificial flowers can be and still be marketed at affordable prices. However, one of the main drawbacks to artificial flowers is that they do not have the pleasing scent and aroma that is ordinarily associated with real flowers. Therefore, there has been and continues to be a need for an artificial flower that is provided with some means that produces or generates a scent or fragrance that simulates living flowers.

SUMMARY OF THE INVENTION

The present invention entails an artificial flower comprising a hollow stem and a flower portion. A fragrance source is associated with the artificial flower and is adapted to emit a fragrance that is directed through at least a portion of a hollow stem.

Further, the present invention entails a method of generating or directing a fragrance that is associated with an artificial flower having a hollow stem and a flower portion. The method entails locating a fragrance source in the vicinity of the flower and causing the fragrance source to emit a fragrance that is directed through at least a portion of a hollow stem.

BRIEF DESCRIPTION OF THE DRAWINGS

FIG. 2 is a sectional view similar to FIG. 1 but with a different fragrance source than that shown in FIG. 1.

FIG. 2A is an enlarged sectional view of a potion of the stem of the artificial flower shown in FIG. 1 having the fragrance source disposed therein.

DESCRIPTION OF EXEMPLARY EMBODIMENTS OF THE INVENTION

Figures 1, 1A:
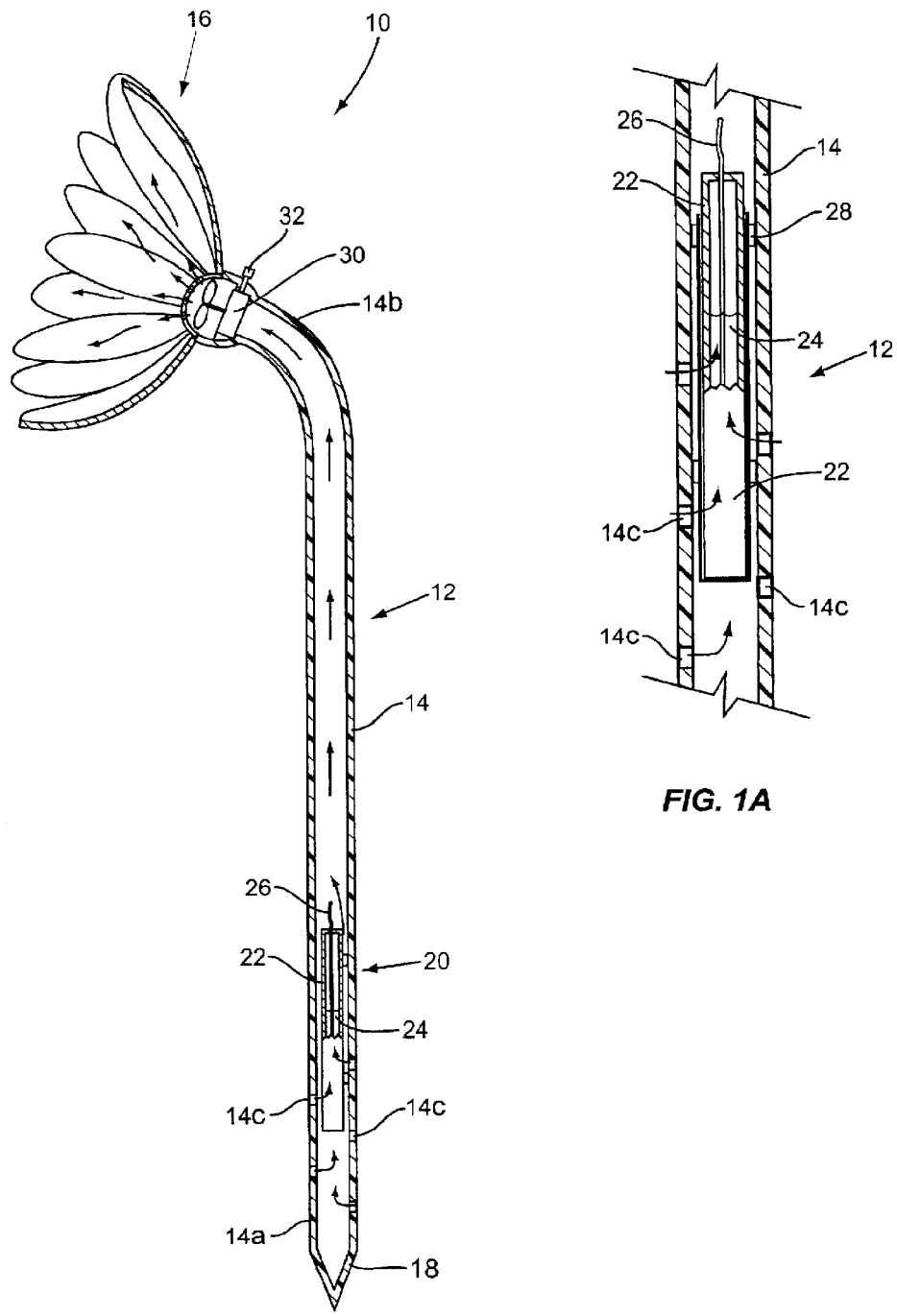
FIG. 1 is a sectional view of the artificial flower of the present invention showing one embodiment of the present invention where a fragrance source is disposed in the hollow stem of the flower.
FIG. 1A is an enlarged fragmentary sectional view of a portion of the stem of the artificial flower having the fragrance source therein.

With further reference to the drawings, the artificial flower of the present invention is shown therein and indicated generally by the numeral 10. The artificial flower includes a hollow stem indicated generally by the numeral 12 and a flower portion 16 secured or extending from the upper portion of the stem 12. The flower of the present invention is referred to as an "artificial flower." In the context of this application, the term "artificial" simply means non-living. Thus, the artificial flower can be made of various materials such as plastics, metal, synthetic materials or could comprise dried flowers or dried vegetation.

As seen in the drawings, the stem 12 is hollow. Stem 12 includes a surrounding wall structure 14 and a lower portion 14a. The lower portion 14a at the stem 12 extends to an anchor end 18. As seen in the drawings, anchor end 18 is formed into a point that permits the artificial flower 10 to be staked or spiked into a support material such as styrofoam, pointing soil, dirt or other supporting structure. Opposite the lower portion 14a is an upper portion 14b. It is noted that the upper portion 14b of the stem 12 is disposed adjacent the flower portion 16. The end of the stem 12 about the upper portion 14b can be open or partially closed. In the embodiment illustrated in the drawings, the end of the upper portion 14b of the stem includes a rounded end that includes a series of openings formed therein. As will be described subsequently herein, the stem is designed such that air and a fragrance can move therethrough and in at least one embodiment is designed such that the fragrance can be emitted or dispersed from the upper end portion 14b of the stem into an area where the flower portion 16 of the artificial flower 10 resides. Also, it is appreciated that the wall structure 14 of the stem can be provided with openings 14c along the length of the stem 12. Again, as will be appreciated from subsequent portions of this disclosure, the openings 14c within the stem may permit air to enter the stem and move upwardly through the hollow stem 12 towards the flower portion 16.

Figures 3, 3A:
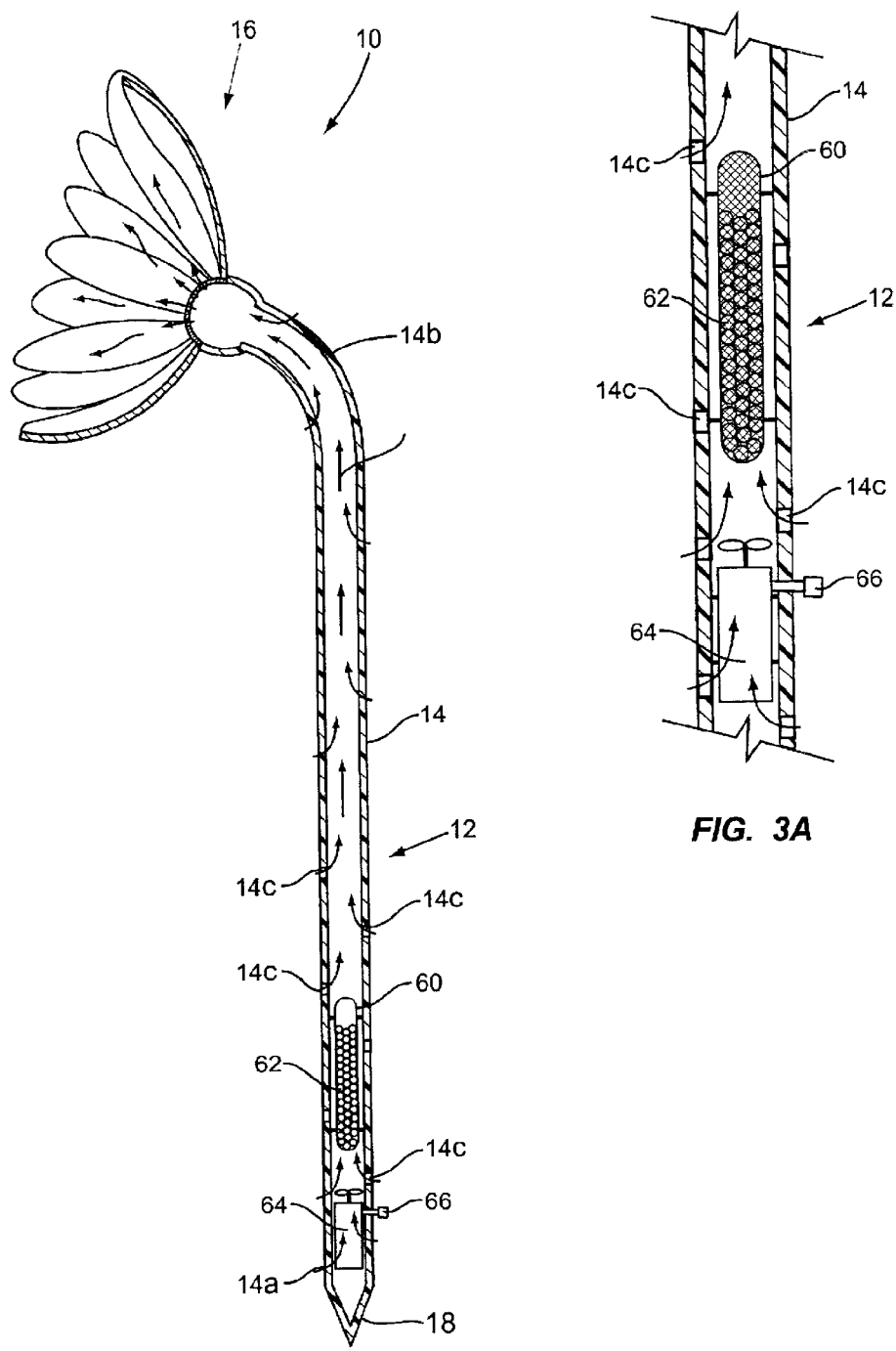
FIG. 3 is a view similar to FIGS. 1 and 2, but illustrating another fragrance source for the artificial flower.
FIG. 3A is an enlarged sectional view of the portion of the stem of the artificial flower shown in FIG. 3 and which shows the fragrance source disposed therein.

The flower portion 16 is disposed adjacent the upper portion 14b of the stem 12. Again, the flower portion 16 forms a part of the artificial flower 10 and in the particular embodiments illustrated herein, the flower portion 16 extends from the upper terminal end portion of the stem. It is appreciated that the flower portion 16 can be secured or integrally formed with the stem through various manufacturing and fabrication techniques. Flower portion 16 can assume various shapes and configurations. In some embodiments, it is contemplated that the flower portion, as illustrated in FIGS. 1–3, would form a generally cup shape and comprise a series of petals.

The present invention entails associating a fragrance source, indicated generally by the numeral 20, with the artificial flower 10. The fragrance source can be of various conventional types and the particular scent emitted by the fragrance source can also vary and can be selected to simulate or mimic the smell or scent of various flowers.

In the embodiment illustrated in FIG. 1, a fragrance source 20 comprises a container 22 having a selected liquid fragrance 24 contained therein. The container 22 is preferably sealed but includes an opening for receiving a wick 26. Wick 26 extends downwardly into the container 22 and includes a portion that is submerged within the liquid fragrance of 24. A portion of the wick 26 extends from the top of the container 22 and is exposed. Container 22 can be disposed in various locations about the artificial flower 10. In the embodiment illustrated in FIG. 1, the container 22 is disposed within the hollow stem 12. Various mounting structures or mounting techniques can be utilized. For example, the container 22 can be set or held in an open mounting structure 28 that is frictionally supported between the interior walls of the stem 12. In the case of the embodiment shown in FIG. 1, the open mounting structure 28 is of an open plastic frame that basically slides into the stem 12 and is frictionally held therein. It may be beneficial in certain embodiments for the mounting structure 28 to be designed such that there is formed at least one air passageway opening between the container 22 and the interior walls of the stem 12. In other words, it will be beneficial in certain embodiments to provide an open space between the container 22 and the interior walls to allow air to pass upwardly around the container 22 and over the wick 26.

In the case of the embodiment shown in FIG. 1, there is provided a fan 30 disposed in the upper end portion 14b of the stem 12. The fan 30 is a battery-powered fan that includes a main body held and supported within the upper portion 14b of the stem and including a fan blade or propeller extending therefrom. A switch 32 extends from the main body of the fan 30 outwardly through a side wall of the stem 12. In the case of the design shown in FIG. 1, the fan 30 is disposed above the fragrance source 20. Therefore, the propeller or fan blade associated with the fan is designed to induce or pull air from below the container 22, past the container 22 and over the wick of 26. The fan causes air to be induced through the openings 14c into the interior of the stem 12. Once in the stem, the induced air is pulled upwardly past the container 22 and the wick 26. Accordingly, fragrance on the saturated or wet wick will be transferred to the passing air and ultimately will be dispersed out the upper portion of the stem 12 adjacent the flower portion 16. Note also that the main body or frame of the fan 30 would be provided with openings that would enable air to be moved or pulled through the upper portion 14b of the stem 12, through the fan structure and out the upper end of the stem to where the fragrance-laden air is dispersed into an area occupied in part at least by the flower portion 16 of the artificial flower.

Turning to FIG. 3, an alternative embodiment for the artificial flower 10 is shown therein. In this case, the fragrance source 20 is in the form of a fragrance block 40. It will be appreciated, that fragrance blocks are known in the air freshener art and therefore details of such will not be submitted herein because those skilled in the art will understand the basic structure and composition of conventional fragrance blocks. In any event, fragrance block 40 is, in the embodiment of FIG. 2, is disposed within the stem 12 of the artificial flower. The fragrance block 40 may assume different configurations. In the case of the embodiment illustrated herein, fragrance block 40 is elongated and round and is in the form of a generally cylindrical shape. Further, fragrance block 40 includes a central opening. Fragrance block 40 is supported in the stem 12 over a heater 42. Heater 42 is battery-powered and includes a switch 48 the extends from the heater 42 out the side wall of the stem 12. A mounting block 44 is disposed over the heater and a heating element 46, such as resistive heating element, extends upwardly from the heater 42 and the mounting block 44 and extends through the central opening formed in the fragrance block 40.

Further, the side wall structure 14 of the stem 12, especially in the area adjacent the position of the fragrance block 40, will includes a series of openings 14c therein to allow air to be induced or to naturally flow into the stem 12. That is, the fragrance block 40 would be preferably spaced inwardly from the wall structure 14 of the stem 12 so as to allow air to pass between the fragrance block 40 and the interior walls of the stem 12. Additionally, a fan, such as shown in FIG. 1, can be positioned below or above the fragrance block to induce air into the stem 12 and pass the fragrance block 40.

When the heater is turned on, the heating element 46 will heat the fragrance block 40 and cause the fragrance block to vaporize and basically produce a vaporizable scent or aroma. As noted above, fragrance blocks in the air freshener art are known. For example, see U.S. Pat. No. 6,289,176, the disclosure of which is expressly incorporated herein by reference.

Turning to FIG. 3, another embodiment of the present invention is shown therein. In this case, the artificial flower 10 is provided with a permeable container 60. The permeable container 60 may assume various forms but in one form the same would comprise a plastic container with openings formed therein to enable air to circulate therethrough. Disposed within the permeable container 60 is an array of fragrance pellets 62. Each fragrance pellet would comprise a fragrance particle or ball and would over time emit a desired fragrance. Preferably the permeable container 60 including the fragrance pellet 62 would be supported within a mounting structure that would be secured in the stem 12. In one embodiment, the mounting structure would be similar to that discussed above with respect to the mounting structure utilized to hold and support the container 22. In any event, the function of the mounting structure would be to hold the permeable container 60 within the stem 12. Preferably the mounting structure would be of an open frame design that would, when inserted within the stem 12, provide an opening around the permeable container 60 to allow air to flow past. In some embodiments, it is foreseen that the permeable container 60 would be frictionally retained or held within the stem 12 and would effectively assume substantially the entire cross section of the stem about a selected length of the stem. In this case, air moving from below the permeable container 60 upwardly would be forced to pass through the permeable container.

In any event, the design of FIG. 3 includes a fan 64 with a propeller or blade associated therewith. Fan 64 in this embodiment is disposed below the permeable container 60 but it is understood that the fan could be oriented in the same manner as indicated in FIG. 1. Fan 64 includes switch 66 that extends outwardly therefrom through the wall structure 14 of the stem 12. Again, as was the case with the fan shown in FIG. 1, fan 64 would be battery-powered and the main body of the fan would be of an open construction that would allow air to be pulled from below the fan, through the open main body of the fan and upwardly through the stem 12.

It is appreciated that the present invention presents an artificial flower that is designed to emit a pleasing fragrance or aroma. A fragrance source 20 is associated with the flower and is designed to emit a fragrance that will be dispersed about the flower. Although the fragrance source can be disposed in various positions and locations with respect to the artificial flower 10, in some embodiments, the fragrance source 20 is disposed in the hollow stem 12 that forms a part of the artificial flower 10. Moreover, the fragrance source may simply be designed or selected to be of the type that will slowly and over a period of time simply emit a fragrance that will move through or from the artificial flower. Dispersion of the fragrance or scent can be enhanced by utilizing heat to heat the fragrance source and/or a fan to pull or push air past the fragrance source.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

What is claimed is:

1. An artificial flower comprising: a hollow stem; a flower portion; a fragrance source disposed within the hollow stem; and a fan disposed within at least a portion of the hollow stem, the fan configured to move air past the fragrance source to direct a fragrance emitted by the fragrance source through at least a portion of the hollow stem.

2. The artificial flower of claim 1 wherein the hollow stem includes a stem portion disposed adjacent the flower portion and wherein the fragrance from the fragrance source is directed through the hollow stem and out the stem portion disposed adjacent the flower portion.

3. The artificial flower of claim 1 wherein the fragrance source includes a container having a liquid fragrance contained therein, and a wick having one portion submerged into the liquid fragrance and another portion extending from the container.

4. The artificial flower of claim 3 wherein the fan moves air past the portion of the wick extending from the container.

5. The artificial flower of claim 4 wherein the fan is disposed between the container having the liquid fragrance and the flower portion of the artificial flower.

6. The artificial flower of claim 5 wherein the stem includes an upper end portion disposed adjacent the flower portion, and wherein the fan is disposed within the upper end portion of the stem.

7. The artificial flower of claim 4 including a mounting structure for holding the container having the liquid fragrance, and wherein the mounting structure supports the container such that there is an open area between the container and the stem such that air may pass through the stem and around the container having the liquid fragrance.

8. The artificial flower of claim 1 wherein the fragrance source includes a fragrance block disposed within the stem of the artificial flower.

9. The artificial flower of claim 8 wherein the stem includes an upper end portion disposed adjacent the flower portion and wherein the fragrance emitted by the fragrance block is dispersed out the upper end of the stem adjacent the flower portion.

10. The artificial flower of claim 1 wherein the fragrance source includes a permeable container having an array of fragrance pellets disposed therein.

11. The artificial flower of claim 10 wherein the permeable container is disposed within the stem of the artificial flower.

12. The artificial flower of claim 10 wherein the fan causes air to be passed over and through the permeable container.

13. The artificial flower of claim 10 wherein the fan directs air through the permeable container, and wherein the permeable container with the fragrance pellets and the fan are disposed such that air directed through the permeable container moves from the permeable container into and through at least a portion of the stem of the artificial flower.

14. A method of generating a fragrance for an artificial flower having a hollow stem and a flower portion, comprising: locating a fragrance source within the hollow stem of the artificial flower, wherein the fragrance source emits a fragrance; locating a fan within at least a portion of the hollow stem; and using the fan to direct the emitted fragrance through at least a portion of the hollow stem.

15. The method of claim 14 wherein the hollow stem includes an upper portion disposed adjacent the flower portion of the artificial plant, and wherein the method includes directing the emitted fragrance through the hollow stem and out the upper portion of the hollow stem adjacent the flower portion.

16. The method of claim 15 wherein air passing the fragrance source in the hollow stem picks up a fragrance from the fragrance source.

17. The method of claim 14 including directing air through the hollow stem with the fan and wherein the air passing through the hollow stem passes over the fragrance source and a fragrance emitted from the fragrance source combines with the air and moves with the air through the stem of the artificial flower.

18. An artificial flower comprising: a hollow stem; a flower portion; a fragrance source disposed within the hollow stem; and a heating source disposed within at least a portion of the hollow stem, the heating source configured to heat the fragrance source to emit a fragrance from the fragrance source and to direct the fragrance through at least a portion of the hollow stem.

19. The artificial flower of claim 18 wherein the heating source is disposed in close proximity to the fragrance source.

20. An artificial flower comprising:
   a hollow stem;
   a flower portion disposed proximate one end of the hollow stem;
   an artificial fragrance source associated with the artificial flower and located remotely from the flower portion, the artificial fragrance source adapted to emit an artificial fragrance; and
   a fan configured to direct air past the artificial fragrance source to combine the air with the artificial fragrance and to move the combined fragrance and air through at least a portion of the hollow stem and out the flower portion.

21. The artificial flower of claim 20 wherein the fan and the artificial fragrance source are disposed adjacent each other.

22. A method of emitting an artificial scent from an artificial flower having a hollow stem, a flower portion, and a fan, the method comprising:
   activating the fan to move air past an artificial fragrance source located remotely from the flower portion and adapted to emit the artificial scent;
   combining the air moving past the artificial fragrance source with the artificial scent emitted from the fragrance source; and
   directing the scented air through at least a portion of the hollow stem and out the flower portion.

* * * * *